United States Patent [19]
Apel

[11] Patent Number: 5,795,751
[45] Date of Patent: Aug. 18, 1998

[54] BIOFILTER FOR REMOVAL OF NITROGEN OXIDES FROM CONTAMINATED GASES UNDER AEROBIC CONDITIONS

[75] Inventor: William A. Apel, Idaho Falls, Id.

[73] Assignee: Lockheed Martin Idaho Technologies Company, Idaho Falls, Id.

[21] Appl. No.: 719,831

[22] Filed: Sep. 30, 1996

Related U.S. Application Data

[63] Continuation-in-part of Ser. No. 255,630, Jun. 9, 1994, abandoned.

[51] Int. Cl.$^6$ .............................. C12P 3/00; C12P 1/04; A61L 9/01
[52] U.S. Cl. ...................... 435/168; 435/170; 435/262.5; 435/266; 55/220
[58] Field of Search ..................... 435/168, 170, 435/262.5, 266, 313; 55/220

[56] References Cited

U.S. PATENT DOCUMENTS

| | | | |
|---|---|---|---|
| 4,173,531 | 11/1979 | Matsch | 210/5 |
| 5,064,763 | 11/1991 | Bentz | 435/266 |
| 5,077,208 | 12/1991 | Sublette | 435/168 |
| 5,378,280 | 1/1995 | Cruze | 106/793 |
| 5,409,834 | 4/1995 | Birowell | 435/310 |

OTHER PUBLICATIONS

Apel, W. A., et al, *The Use of Denitrifying Bacteria for the Removal of Nitrogen Oxides from Combustion Gases*, Fuel vol. 72, pp. 1715–1718 (1993).

Ye, R. W., et al, *Denitrification Production: and Consumption of Nitric Oxide*, Applied and Environmental Microbiology, vol. 60, No. 4, pp. 1053–1058 (1994).

Wood, S. C., *Select the Right $NO_x$ Control Technology*, Chemical Engineering Progress, pp. 32–38, (Jan. 1994).

Cho, S. M., *Properly Apply Selective Catalytic Reduction for $NO_x$ Removal*, Chemical Engineering Progress, pp. 39–45 (Jan. 1994).

Garg, A., *Specify Bettery Low-$NO_x$ Burner for Furnaces*, Chemical Engineering Progress, pp. 46–49, (Jan. 1994).

Primary Examiner—Leon B. Lankford, Jr.
Attorney, Agent, or Firm—Alan D. Kirsch

[57] ABSTRACT

A biofilter for reducing concentrations of gaseous nitrogen oxides in a polluted gas comprises a porous organic filter bed medium disposed in a housing, the filter bed medium including a mixed culture of naturally occurring denitrifying bacteria for converting the nitrogen oxides to nitrogen gas, carbon dioxide, and water. A method of reducing concentrations of nitrogen oxides in polluted gas comprises conducting the polluted gas through the biofilter so that the denitrifying bacteria can degrade the nitrogen oxides. A preferred filter medium is wood compost, however composts of other organic materials are functional. Regulation of pH, moisture content, exogenous carbon sources, and temperature are described.

31 Claims, 6 Drawing Sheets

BIOFILTER FOR REMOVAL OF NITROGEN OXIDES FROM CONTAMINATED GASES UNDER AEROBIC CONDITIONS

CROSS-REFERENCE TO RELATED APPLICATIONS

This is a continuation-in-part of application Ser. No. 08/255,630, filed Jun. 9, 1994, now abandoned.

CONTRACTUAL ORIGIN OF THE INVENTION

The United States Government has rights in this invention pursuant to Contract No. DE-AC07-76ID01570 between the United States Department of Energy and EG&G Idaho, Inc.

BACKGROUND OF THE INVENTION

This invention relates to a device and a method for removing pollutants from contaminated gases. More particularly, this invention relates to a device and method for removing gaseous nitrogen oxides from fossil-fired power plant emissions and the like.

Various industries, including those involving coal-fired electrical power generation, wood processing, and oil and gas production, produce nitrogen oxide gases (e.g., NO, $N_2O$, $NO_2$, and $N_2O_4$). Nitrogen oxides (collectively referred to as $NO_x$) are primary air pollutants and, as such, provoke considerable interest in the development of efficient, cost effective technologies to remediate $NO_x$-containing emissions. $N_2O$ is thought to be a major contributor to global warming due to its persistence in the atmosphere (about 150 years) and its relatively high infrared absorbance (>200 times that of carbon dioxide). William A. Apel & Charles E. Turick, *The Use of Denitrifying Bacteria for the Removal of Nitrogen Oxides from Combustion Gases*, 72 Fuel 1715 (1993). $N_2O$ concentrations in the atmosphere have been increasing at a rate of 0.2 to 0.3% per year for at least 20–30 years. Rick W. Ye et al., *Denitrification: Production and Consumption of Nitric Oxide*, 60 Appl. Envir. Microbiol. 1053 (1994). NO and $N_2O$ are major contributors to atmospheric ozone destruction. Moreover, $N_2O$, NO, and $NO_2$ can undergo a number of other deleterious reactions in the atmosphere involving ozone, and can also lead to production of atmospheric nitric acid and acid rain.

Many microorganisms are capable of removing or chemically converting one or more of these $NO_x$ compounds to harmless products. Microbially catalyzed reactions involving the reduction of nitrite ($NO_2$) to nitric oxide (NO), NO to nitrous oxide ($N_2O$), and the further reduction of $N_2O$ to nitrogen gas ($N_2$) are well documented. Most of these reductive reactions are contributions to the process component of the nitrogen cycle called denitrification, wherein nitrate ($NO_3^-$) and nitrite ($NO_2^-$) anions are ultimately reduced to $N_2$ gas.

Denitrifying microbes are a phylogenetically diverse group, including species from such genera as Pseudomonas, Paracoccus, Flavobacterium, Thiobacillus, Hyphomicrobium, Azospirillum, Alcaligenes, Nitrosomonas, Achromobacter, and Halobacterium. These denitrifying bacteria display extreme diversity of ecological niches and nutritional requirements. While most denitrifying bacteria can grow either aerobically or anaerobically, they are generally believed to be capable of $NO_x$ reduction only under anaerobic conditions.

Until recently, denitrification had been thought to be an obligately anaerobic, respiratory process with NOx functioning as a terminal electron acceptor. U.S. Pat. No. 5,077,208 to Sublette describes a process of converting nitric oxide in a gas stream to elemental nitrogen by contacting the gas stream under anaerobic conditions with a slurry containing a pure culture of the denitrifying bacterium, *Thiobacillus denitrificans*, and a culture medium containing an energy source for the bacterium and no terminal electron acceptor except nitric oxide. This anaerobic process cannot be applied to removing nitric oxide from ordinary combustion gas streams, which typically contain 2.5–5% oxygen, without first removing or controlling oxygen levels. Also, the inefficient transfer of gases between the slurry and the gas stream is another disadvantage for high removal rates. Further, the need to inoculate with and maintain pure cultures of *Thiobacillus denitrificans* is yet another disadvantage.

In view of the foregoing, it will be appreciated that a process of removing nitrogen oxides from gas streams wherein the process functions under both aerobic and anaerobic conditions, employs a more favorable system of transfer of gases, and enjoys the simple robustness and high level of metabolic activity offered by naturally occurring mixed cultures of microbes would be a significant advancement in the art.

OBJECTS AND SUMMARY OF THE INVENTION

It is an object of the present invention to provide a device and a method for removing gaseous nitrogen oxides from polluted gases such as combustion gases and the like.

It is also an object of the invention to provide a device and a method using denitrifying microorganisms for removing gaseous nitrogen oxides from polluted gases that can contain up to about 5% oxygen, such as combustion gases and the like.

It is another object of the invention to provide a device and a method using naturally occurring mixed cultures of denitrifying microorganisms for removing gaseous nitrogen oxides from oxygen-containing polluted gases, such as combustion gases and the like.

It is still another object of the invention to provide a device and method of removing gaseous nitrogen oxides from polluted gases using biologically active filters.

It is yet another object of the invention to provide a device and method for removing gaseous nitrogen oxides from polluted gases using a system of improved transfer of gases between the polluted gases and a biologically active component that removes the nitrogen oxides therefrom.

These and other objects are achieved by providing a biofilter for producing a denitrified gas from a gas stream containing nitrogen oxides comprising a housing including an inlet for conducting the nitrogen oxide-containing gas stream into the biofilter and an outlet for conducting the denitrified gas stream out of the biofilter; and a porous organic filter bed medium disposed in the housing such that the nitrogen oxide-containing gas stream passes through the bed medium for denitrification before being conducted through the outlet, the bed medium including a mixed culture of naturally occurring denitrifying bacteria for converting the nitrogen oxides to nitrogen gas, carbon dioxide, and water. A preferred bed medium comprises a compost selected from organic matter such as wood, leaves, grass clippings, or the like, or mixtures thereof. The bed medium can further contain peat, clay, soil, wood chips, wood bark, or the like, or mixtures thereof. The biofilter may optionally further include a sealable filling port for adding a liquid to the compost and a sealable drain port for draining excess liquid from the compost. The housing can be composed of a substantially gas tight material and can be constructed to substantially prevent leakage of gas through the housing.

A method of producing a denitrified gas from a gas stream containing nitrogen oxides comprises the steps of:

(a) providing a biofilter comprising
   a housing including an inlet for conducting the nitrogen oxide-containing gas stream into the biofilter and an outlet for conducting the denitrified gas out of the biofilter, and
   a porous organic filter bed medium disposed in the housing, the bed medium including a naturally occurring mixed culture of denitrifying bacteria capable of converting the nitrogen oxides to nitrogen gas, carbon dioxide, and water;

(b) conducting the nitrogen oxide-containing gas stream into the biofilter through the inlet so that the gas stream passes through the filter bed medium wherein the denitrifying bacteria convert the nitrogen oxides to nitrogen gas, carbon dioxide, and water thereby producing a denitrified gas; and (c) conducting the denitrified gas out of the biofilter through the outlet. A preferred bed medium comprises a compost selected from organic matter such as wood, leaves, grass clippings, or the like, or mixtures thereof. The bed medium can further comprise peat, clay, soil, wood chips, wood bark, or the like, or mixtures thereof. Moisture lost from the biofilter due to the passage of the gas stream through the compost is replenished periodically by addition of a liquid, such as a buffer solution, to the compost. The buffer solution also can be used for maintaining the pH of the compost in the range of pH 6–8, where the denitrifying bacteria are most active in degrading $NO_x$ to non-toxic products. External controls can also be used to regulate pH, such as addition of acid or base to the bed medium. Addition of a carbon source, especially a non-fermentable carbon source such as lactate, is also beneficial to reducing $NO_x$ concentrations. Preferably, the amount of the carbon source added to the biofilter is the carbon equivalents necessary to completely convert the $NO_x$ to $N_2$, $CO_2$, and $H_2O$. The temperature of the biofilter is preferably maintained at 15°–60° C., and more preferably at 22°–37°C., for reducing $NO_x$ concentrations. Further, the biofilter is functional in both aerobic and anaerobic environments, and the range of oxygen contents of the $NO_x$-containing gas is preferably up to about 5%.

DETAILED DESCRIPTION OF THE INVENTION

Before the present device and method for removal of gaseous nitrogen oxides from polluted gases are disclosed and described, it is to be understood that this invention is not limited to the particular process steps and materials disclosed herein as such process steps and materials may vary somewhat. It is also to be understood that the terminology used herein is used for the purpose of describing particular embodiments only and is not intended to be limiting since the scope of the present invention will be limited only by the appended claims and functional equivalents thereof.

It must be noted that, as used in this specification and the appended claims, the singular forms "a," "an," and "the" include plural referents unless the content clearly dictates otherwise. Thus, for example, reference to "a biofilter" includes reference to two or more biofilters, reference to "a port" includes reference to two or more ports, and reference to "an inlet" includes reference to two or more inlets.

In describing and claiming the present invention, the following terminology will be used in accordance with the definitions set out below.

As used herein, "biofiltration" means the venting of contaminated air, vapors, or gases through a biologically active material. A "biofilter" is a device containing a biologically active material or component through which contaminated gases, vapors, or air are vented for reducing amounts or concentrations of one or more contaminants or pollutants from the gases, vapors, or air.

As used herein, "denitrification" is the process of reducing oxidized forms of nitrogen, such as $NO_x$, to nitrogen gas ($N_2$). "Denitrifying bacteria" are bacteria that reduce oxidized nitrogen compounds, particularly $NO_x$, to molecular nitrogen.

As used herein, "glucose" means D-glucose.

As used herein, "removing," "removal," and similar terms mean completely or partially eliminating. Thus, in the context of controlling gaseous nitrogen oxides in polluted gases, removing nitrogen oxides comprises partially or completely denitrifying $NO_x$ gases, thereby either reducing or eliminating their concentrations.

As used herein, "gas" means gas, vapor, or air. "Denitrified gas" means any gas initially containing $NO_x$ concentrations from which the $NO_x$ concentration has been either reduced or eliminated.

The present invention is drawn to a device and a method for removing nitrogen oxides or reducing nitrogen oxide concentrations in gases polluted with nitrogen oxides. In the device and process, contaminated gases are conducted through a biofilter comprising a porous organic filter bed medium. As these gases flow through the bed medium, $NO_x$ is metabolically converted to non-toxic products, $N_2$, $CO_2$, and $H_2O$, by a naturally occurring mixed culture of denitrifying bacteria that resides in the bed medium, thereby resulting in the production of a denitrified gas.

Biofilter

Figure 1:
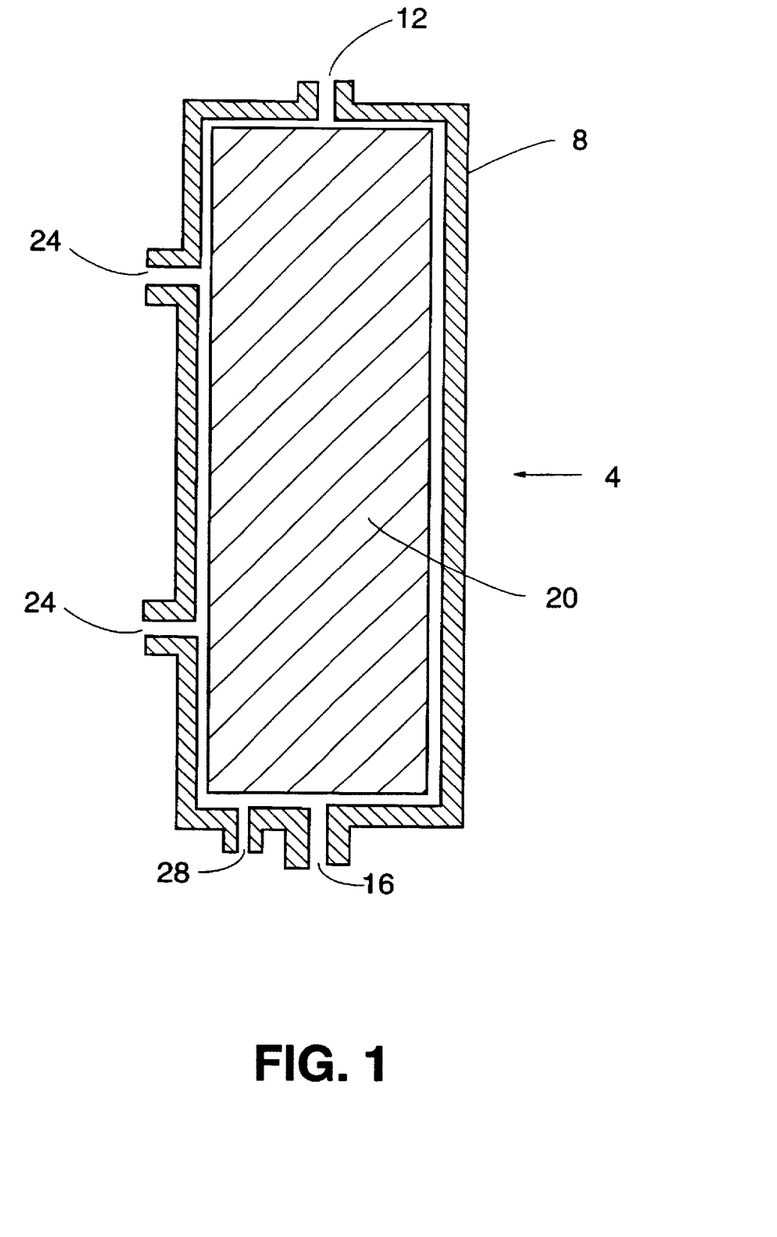
FIG. 1 shows an side sectional view of an illustrative embodiment of a biofilter according to the present invention.

FIG. 1 shows an illustrative embodiment of a biofilter according to the present invention. The biofilter 4 comprises a housing 8 including an inlet opening 12 and an outlet opening 16. A $NO_x$-containing gas stream from which $NO_x$ is to be removed is conducted into the biofilter 4 through the inlet 12 by means of a hose, pipe, or the like joined to the inlet 12 in a conventional manner. After passing through the biofilter 4, the denitrified gas exits through the outlet 16, which can also be joined to a hose, pipe, or the like, for venting to the atmosphere or for further treatment. The housing 8 is preferably composed of a substantially gas tight material and is constructed to minimize or prevent leakage of gases into or out of the biofilter 4. The housing 8 is filled with a porous organic filter bed medium 20 containing a naturally occurring mixed culture of denitrifying bacteria. The $NO_x$-gas stream entering the biofilter 4 through the inlet 12 passes through the pores of the filter bed medium 20 so that the gas, including $NO_x$, comes into contact with the denitrifying bacteria. The denitrifying bacteria convert the $NO_x$ into nitrogen gas, carbon dioxide, and water. These non-toxic products can then be removed from the biofilter. For convenience in operating the biofilter 4, one or more filling ports 24 are optionally constructed in the wall of the housing 8 for adding water, buffer, carbon source, and the like to the filter bed medium 20 or removing gas samples for analysis. Further, one or more drain ports 28 are optionally constructed in the wall of the housing 8 for draining excess water or other liquids. Both the filling ports 24 and the drain ports 28 are sealable to keep the biofilter substantially gas tight when the ports are not in use. The filling ports 24 and drain ports 28 can be opened when necessary, for example to take samples, add buffer, or drain excess liquid, and can be resealed.

Effect of Hydration and Biofilter Configuration on $NO_x$ Removal

In initial experiments, biofilters were constructed from glass process pipe (3 inches×36 inches) packed with 3 1 of a coniferous wood compost/wood chip bed medium. This compost was obtained from the Schenectady County Soil and Water Conservation District (Scotia, N.Y.). Composts derived from other organic materials, such as leaves, grass clippings, and the like, and mixtures thereof, are also functional. These compost materials provide a porous support medium for the naturally occurring mixed culture of denitrifying bacteria and allow a high rate of gas flow through the biofilter and gas exchange between the gas stream and the bacteria. Other types of ingredients can also be added to and mixed with the compost, including peat, clay, soil, wood chips, wood bark, and the like, and mixtures thereof.

Nitrogen ($N_2$) gas streams containing selected amounts of nitric oxide (NO) were conducted through the biofilters at a rate of 1 l/min. The biofilters were treated daily with a phosphate buffer solution to provide moisture to the compost and maintain a neutral pH.

Three biofilters were prepared according to this configuration. Biofilter 1.0 was maintained at 37° C. and treated with 0.6 mM $K_2HPO_4$ buffer. Biofilter 2.0 was maintained at 37° C. and treated with 0.6 mM $K_2HPO_4$ buffer containing 1% (w/v) glucose. Biofilter 3.0 was maintained at room temperature (about 22° C.) and treated with 0.6 mM $K_2HPO_4$ buffer containing 1% (w/v) glucose. Over a three week period, gas streams (1 l/min) containing 100 µl/l of NO were conducted through each of these three biofilters. At various times, influent and effluent gas samples were removed from each biofilter and analyzed for NO content using an $NO_x$ chemiluminescent analyzer. This analyzer was a Bendix Model 8101-C Oxides of Nitrogen Analyzer (Dasibi Environmental Corp., Glendale, Calif.) modified to allow flow injection of NOX. During this experiment, 77–100%, 79–99%, and 62–68% of the NO in the influent streams were removed by Biofilters 1.0, 2.0, and 3.0, respectively. Following these studies, influent NO concentrations were increased to 250 µl/l. Fourteen days after this increase, 51%, 62%, and 32% of influent NO were removed from Biofilters 1.0, 2.0, and 3.0, respectively.

During the course of these experiments, drying of the compost or filter bed medium occurred due to the flow of the gas stream through the biofilter, and moisture was replenished by quickly pumping buffer solutions through the biofilters. To determine if this hydration technique was adequate, the effect of adding moisture and exogenous carbon to the compost was assessed. First, the concentrations of NO in the effluent gas streams of Biofilters 1.0 and 2.0 were measured. Next, each of these two biofilters was treated with 80 ml of either 0.6 mM $K_2HPO_4$ buffer (Biofilter 1.0) or 0.6 mM $K_2HPO_4$ buffer containing 1% (w/v) glucose (Biofilter 2.0). These solutions were added to the bed medium in 10 ml aliquots through ports located every 3 inches along the lengths of the biofilters. The influent gas streams to these two biofilters each contained 238 µl/l of NO. Six hours following the hydration treatments, the concentrations of NO in the effluent streams decreased from 139 µl/l to 89 µl/l for Biofilter 1.0 and from 81 µl/l to 12 µl/l for Biofilter 2.0. Twenty-four hours following hydration, the NO concentrations in the effluent streams contained 118 µl/l in Biofilter 1.0 and 2 µl/l in Biofilter 2.0. These results indicated that the hydration technique did not adequately provide moisture and glucose to all sections of the compost. Thus, shorter biofilters were constructed and evaluated for moisture distribution.

A shorter biofilter (Biofilter 2.1) was constructed from a 12 inch length of glass process pipe (3 inch diameter) and was packed with 1.4 liters of the bed medium from Biofilter 2.0. At the time the bed medium was transferred, Biofilter 2.0 was removing 94% of the NO in an influent gas stream containing 250 µl/l NO. Moisture and glucose (50 ml of 0.6 mM $K_2HPO_4$, 1% (w/v) glucose) were delivered daily through two filling ports. After 3 days of operation, 99% of the NO in an influent gas stream containing 248 µl/l NO was being removed. In addition, a significant improvement in moisture distribution was observed visually. As a consequence, Biofilters 1.0 and 3.0 were converted to the shorter, more efficient design (Biofilters 1.1 and 3.1, respectively) and all subsequent experiments were conducted using this design. Biofilters 1.1, 2.1, and 3.1 continued to receive exposure to the same temperature conditions and hydrating solutions as their respective predecessor biofilters had received.

The NO level in the influent gas streams of the newly configured biofilters was then raised from 250 µl/l to 500 µl/l. After one week of operation at the higher level of NO, Biofilters 1.1, 2.1 and 3.1 were removing 38%, 74%, and 57% of the influent NO, and moisture levels appeared adequate. Therefore, adequate hydration of the filter medium is important for removing high levels of $NO_x$ from polluted gas streams, probably because the denitrifying bacteria need water for growth and metabolism.

Effect of Glucose Concentration on $NO_x$ Removal

Studies were initiated to determine the effect of increased glucose concentration on $NO_x$ removal by biofilters according to the present invention. Biofilter 2.1 was treated with 50 ml of a solution containing 0.6 mM $K_2HPO_4$ and 2% (w/v) glucose, an increase of 1% glucose from the previous treatment solution. Twenty-four hours after receiving this increased glucose treatment, Biofilter 2.1 removed 98% of influent NO being introduced at 545 µl/l. Biofilter 2.1 was then treated daily with 50 ml of a solution containing 0.6 mM $K_2HPO_4$ and 2% (w/v) glucose. On days 2 and 3 of the experiment, 99% NO removal was measured. Thus, providing a carbon source to the filter medium improves performance of the naturally occurring mixed culture of denitrifying bacteria in the filter bed medium. Preferred carbon sources include glucose and molasses.

Effect of pH on $NO_x$ Removal

Figure 2:
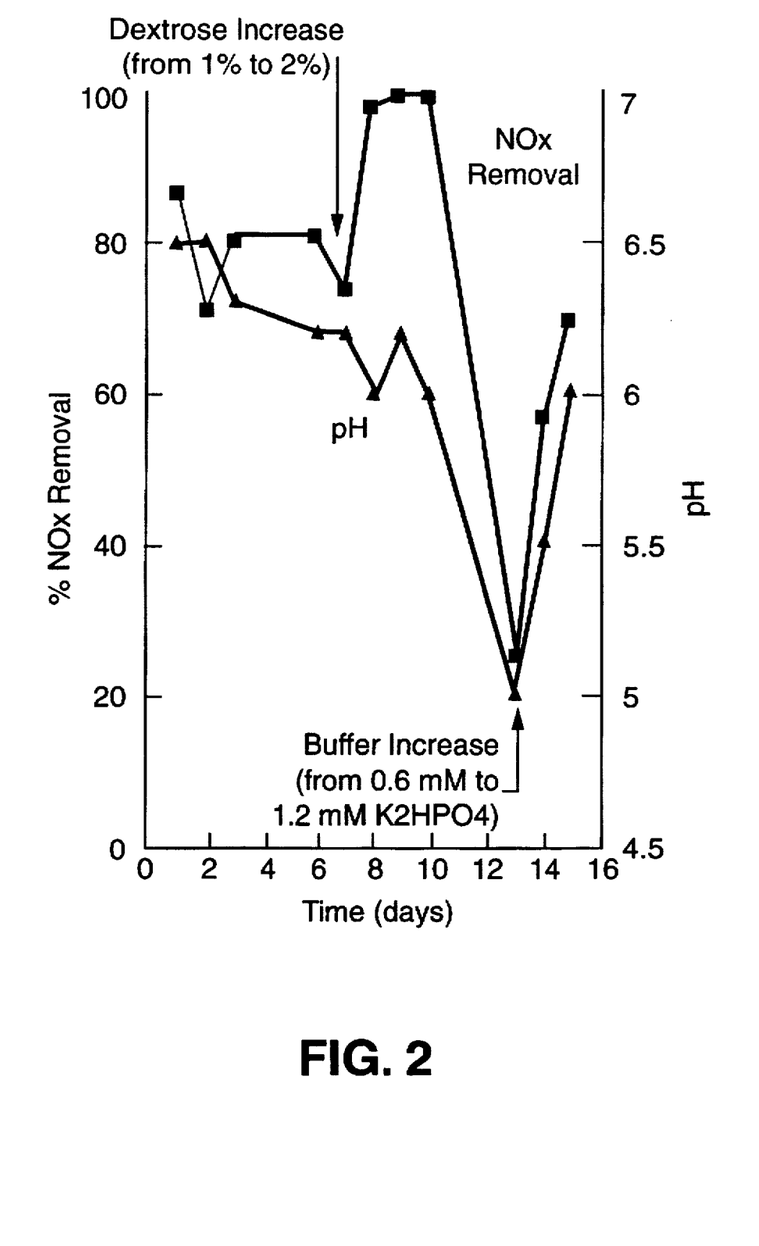
FIG. 2 shows a graphic representation of the relationship between pH and removal of $NO_x$ from a polluted gas in one illustrative embodiment of the present invention, wherein ■=% $NO_x$ removal; ▲=pH; ↓=time of increase of added glucose from 1% to 2%; and ↑=time of increasing buffer concentration from 0.6 mM to 1.2 mM.

Six days after the glucose concentration provided by daily administration of 50 ml of hydration solution to Biofilter 2.1 was raised to 2%, the removal of NO from the influent gas stream dropped to 25%. The pH of liquid draining from the biofilters was monitored regularly. Prior to raising the glucose concentration to 2%, the pH of Biofilter 2.1 ranged from 6.3 to 6.5. As shown in FIG. 2, after the glucose level was increased, the pH initially remained stable, but then dropped to about pH 5.0. This decrease in removal of NO from the influent gas stream was concomitant with the decrease in pH.

Removal of $NO_x$ in the biofilters is due to the activity of the naturally occurring mixed culture of denitrifying bacteria. Although denitrifying bacteria can tolerate some pH variance, they are metabolically most active when the pH of their environment ranges between pH 6 and pH 8. To determine if the drop in pH was related to the sharp decrease in efficiency of NO removal, Biofilter 2.1 was treated with a stronger buffer, 1.2 mM $K_2HPO_4$. As shown in FIG. 2, 24 hours after the buffering capacity of the hydration solution was increased, increases in both the pH of the solution draining from the biofilter and removal of NO from the influent gas stream were observed. Within 48 hours, the pH of the liquid draining from the biofilter measured 6.0 and NO removal was 70%.

Figure 3:
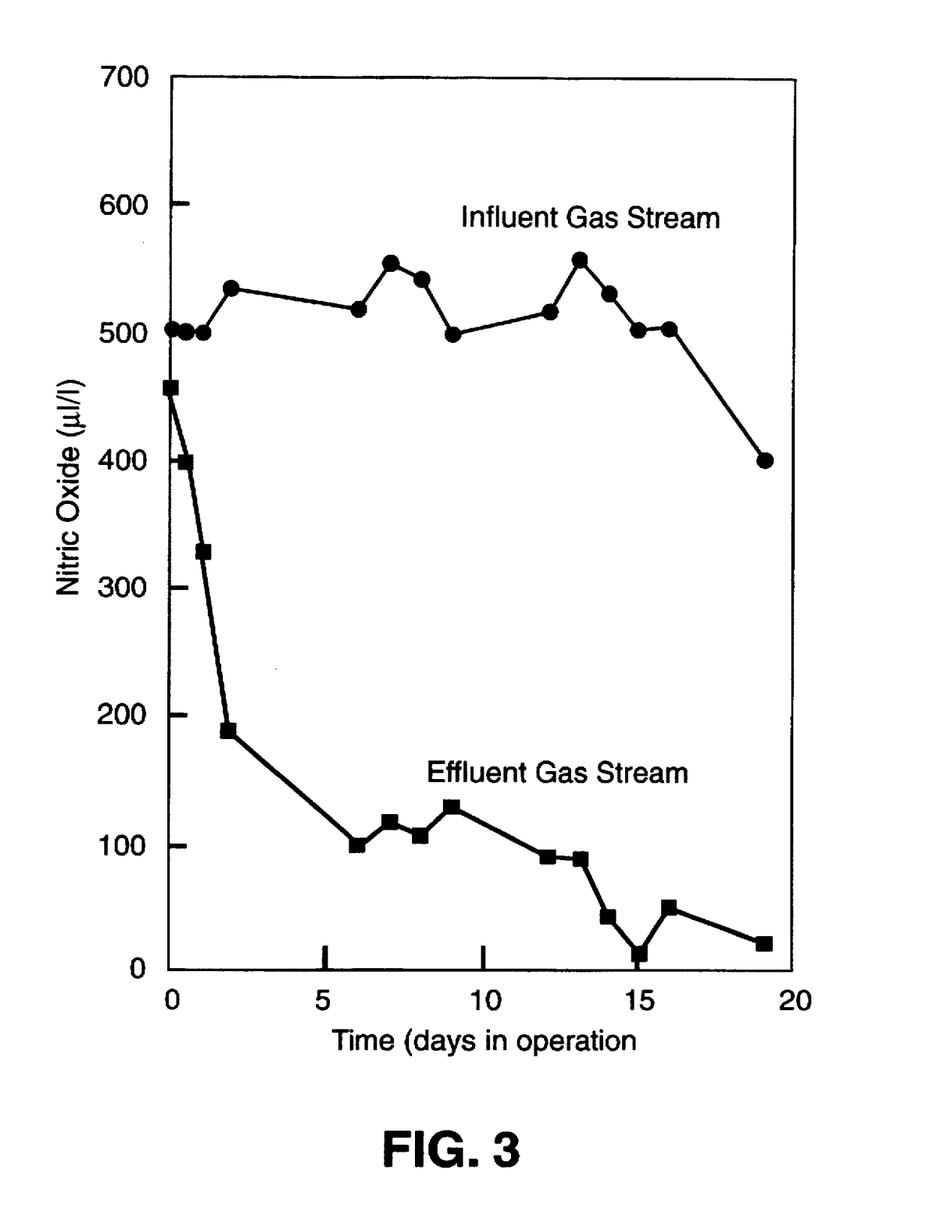
FIG. 3 shows a graphic representation of the effect of pH control on removal of $NO_x$ from a polluted gas in one illustrative embodiment of the present invention, wherein ●=influent NO concentration and ■=effluent NO concentration.

To confirm the effect of pH on $NO_x$ removal, Biofilter 4.0 was prepared with fresh bed medium, comprising wood compost treated with 2% glucose and maintained at pH 6.5. The biofilter was maintained at room temperature (about 22° C.) and treated daily with 50 ml of a solution containing 1.2 mM $K_2HPO_4$, 2% (w/v) glucose, and the initial influent gas stream contained about 500 µl/l of NO. As shown in FIG. 3, NO levels in the effluent gas stream decreased from 457 µl/l to 96 µl/l within 6 days. Following 19 days of operation, 95% of influent NO was removed. These results indicate that pH control in the biofilter is a critical parameter for efficient removal of $NO_x$. The pH of the biofilters is preferably maintained in the range of pH 6 to pH 8.

Effect of Carbon Source and Temperature on $NO_x$ Removal

Although a mixed consortium of bacteria is naturally present in the bed medium, degradation of $NO_x$ in the biofilter is primarily due to the activity of a mixed culture of denitrifying bacteria. The majority of the denitrifying bacteria are non-fermenters. However, under the anaerobic conditions of the biofilters described above, a portion of the bacterial consortium ferments glucose. Metabolic end products of glucose fermentation such as lactic acid, acetic acid, and formic acid accumulate in the bed medium and cause a decrease in the pH, thus inhibiting denitrification.

Figure 4:
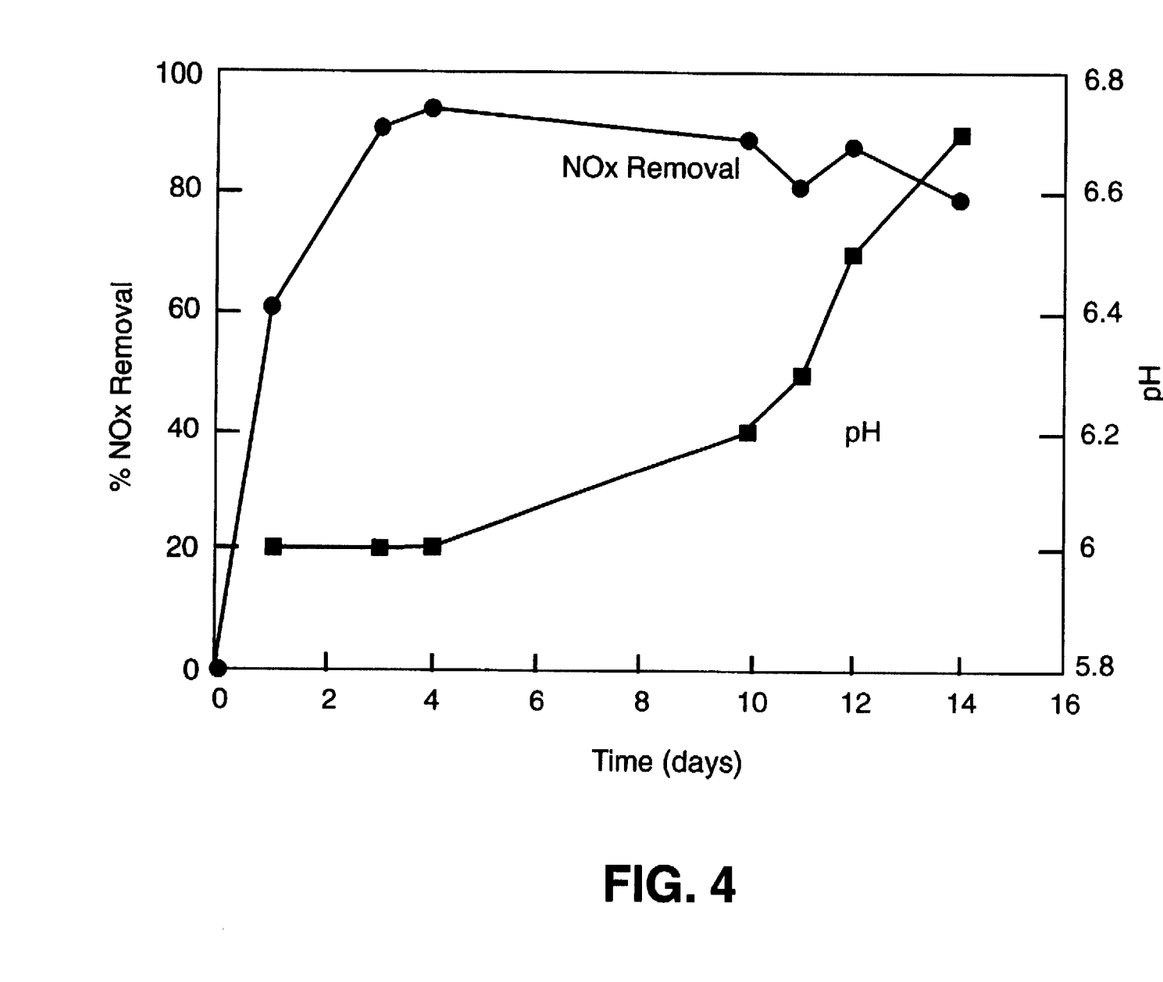
FIG. 4 shows a graphic representation of the effect on pH and $NO_x$ removal of amendment of the filter medium with a non-fermentable carbon source according to the present invention, wherein ●=% $NO_x$ removal and ■=pH.

To avoid the pH changes due to accumulation of fermentative end products, use of a non-fermentable carbon source was evaluated. Biofilter 5.0 containing fresh bed medium comprising wood compost was constructed, maintained at 37° C., and treated daily with 45 ml of a solution containing 0.3 mM $K_2HPO_4$ and 0.13M lactate. The initial influent gas stream contained 500 µl/l NO delivered at a rate of 1 l/min. As shown in FIG. 4, within 4 days of operation, 94% of NO removal was measured. Over a 14 day test period, NO removal in the biofilter ranged from 79 to 94%. Initially, the pH of the liquid draining from the compost was approximately pH 6, however, after 5 days the pH gradually increased to about pH 6.7 at day 14. Although the pH values measured in the biofilter during this test period remained in the range compatible with denitrification, the data indicate that for long-term operation, external pH control may be required.

External pH control can be effected directly by treating the biofilter with acidic (e.g., lactic acid, phosphoric acid) or basic (e.g., potassium phosphate) solutions. Another method of controlling pH is adding ground calcite (calcium carbonate) to the bed medium. Calcite is a solid alkaline material that is solubilized by acid. Mixing ground calcite directly in the bed medium continuously neutralizes metabolic end products of sugar fermentation, such as lactic acid, acetic acid, and formic acid.

Additional studies measuring the effects of lactate and temperature on microbial reduction of $NO_x$ in compost biofilters were conducted. Three additional biofilters (Biofilters 6.0, 7.0, and 8.0) each containing 1.4 l of fresh bed medium comprising wood compost/wood chip mixture were constructed. Nitrogen gas streams containing various concentrations of NO (100–500 µl/l) were conducted through these biofilters at a rate of 1 l/min. The carbon equivalents ($CH_2O$) required by bacteria to completely convert the level of NO present in the influent gas streams to nitrogen gas, carbon dioxide, and water were calculated. Two moles of NO are biologically converted for every mole of $CH_2O$. For example, 16 mM $CH_2O$/day is required by bacteria to completely convert an inlet NO concentration of 32 mM NO/day (500 µl/l of NO purged through a biofilter at a rate of 1 l/min). Based on this calculation, the quantity of lactate in the buffer solutions added daily to the biofilters was adjusted as inlet NO levels increased. To control pH, the biofilters were each treated daily with 60 ml of a solution containing 0.04M $Na_2HPO_4$ and 0.02M $KH_2PO_4$. Biofilters 6.0, 7.0, and 8.0 were initially exposed to a flow of gas containing 100 µl/l of NO. The concentration of NO was increased to 250 µl/l on day 10 and 500 µl/l on day 25 of the experiment. NO levels present in the influent and effluent gas streams were measured over a 42 day test period, shown in FIG. 5.

Figure 5:
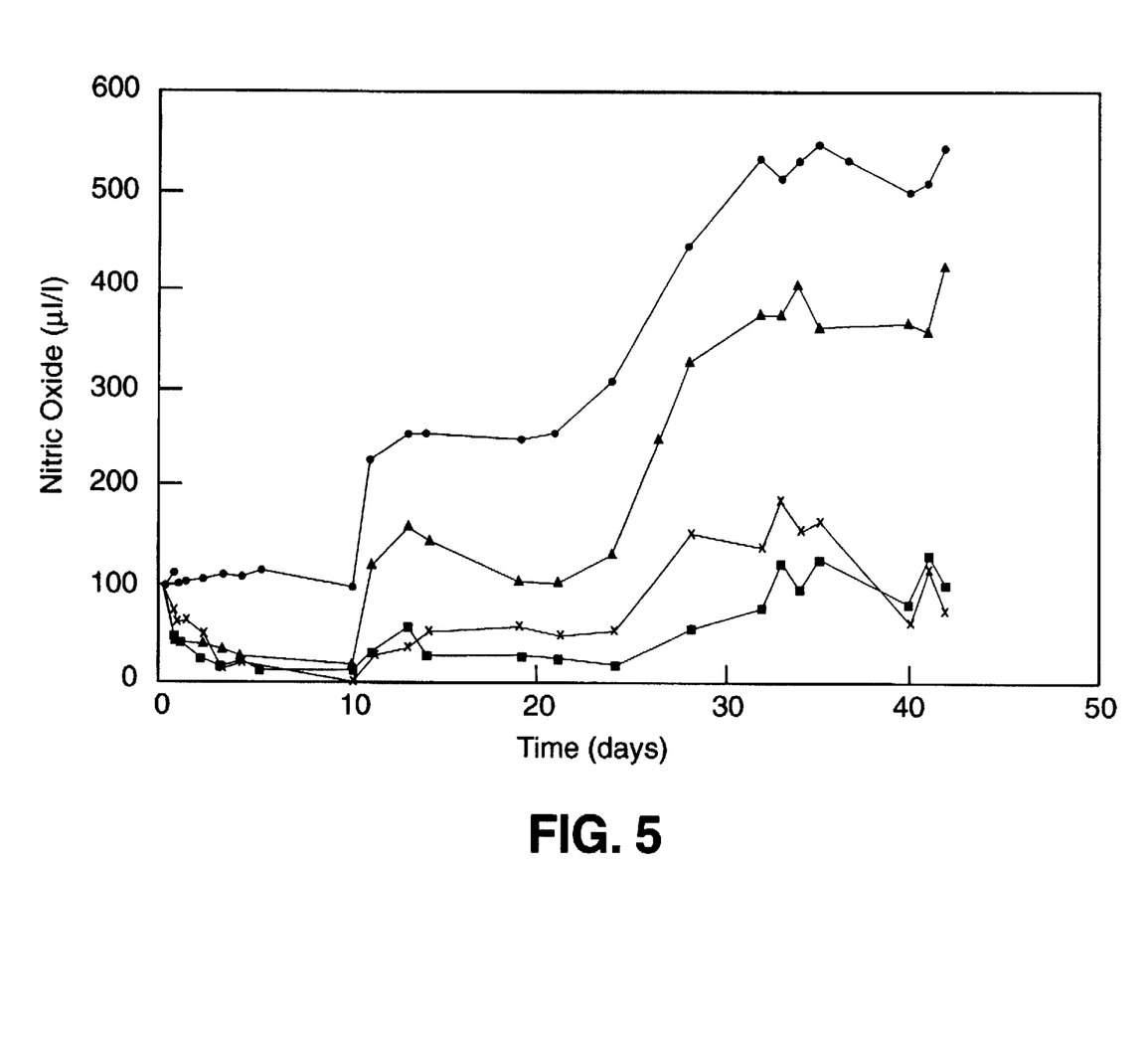
FIG. 5 shows the effect of a non-fermentable carbon source and temperature on $NO_x$ removal from a polluted gas according to the present invention, wherein ●=inlet NO concentration; ■=outlet NO concentration from Biofilter 6.0; ▲=outlet NO concentration from Biofilter 7.0; and *=outlet NO concentration from Biofilter 8.0.

The effect of temperature on $NO_x$ removal was measured in Biofilters 6.0 and 8.0. Biofilter 6.0 was maintained at 37° C. and Biofilter 8.0 was maintained at 22° C. Both biofilters were treated daily with 60 ml of 0.04M $Na_2HPO_4$, 0.02M $KH_2PO_4$, and the calculated amount of lactate needed to completely convert NO to $N_2$, $CO_2$, and $H_2O$. Initially, higher NO removal occurred at 37° C., however, microbial activity at 22° C. increased with time. By day 3, about 85% of the influent NO was removed by both Biofilter 6.0 and 8.0. As shown in FIG. 5, at influent concentrations of 250 µl/l of NO (days 10–24) and 500 µl/l (days 25–42) NO removal was comparable. At an influent NO level of 250 µl/l, Biofilter 6.0 removed 94% of the influent NO and Biofilter 8.0 removed 83% of influent NO. At an influent concentration of 500 µl/l of NO, Biofilter 6.0 removed 83% of influent NO and Biofilter 8.0 removed 87% of influent NO.

The effect of lactate as a carbon source on reduction of $NO_x$ levels also was measured in Biofilters 6.0 and 7.0.

Biofilter 6.0 was treated daily with 60 ml of 0.04M $Na_2HPO_4$, 0.02M $KH_2PO_4$, and the calculated amount of lactate needed to completely convert NO to $N_2$, $CO_2$, and $H_2O$, and Biofilter 7.0 was treated daily with 60 ml of 0.04M $Na_2HPO_4$, 0.02M $KH_2PO_4$. Both biofilters were maintained at 37°. At an influent NO concentration of 100 µl/l, the addition of exogenous carbon to the biofilter did not result in a notable increase in NO degradation. On day 10, 12 µl/l NO (88% NO removal) was measured in the effluent gas stream of Biofilter 6.0 and 19 µl/l NO remained (80% NO removal) in the effluent stream of Biofilter 7.0. As NO levels were increased to 250 µl/l and 500 µl/l, lactate treatment significantly increased microbial degradation of NO in this biofilter. After operating for 14 days at an influent NO level of 250 µl/l, 94% NO removal was measured by Biofilter 6.0, and 58% NO removal was measured by Biofilter 7.0. On day 42, 83% of the influent NO (507 µl/l) was removed by Biofilter 6.0, and 22% NO was removed by Biofilter 7.0. Thus, at higher NO, levels, addition of a nonfermentable carbon source to the biofilter improved removal of $NO_x$ from influent gas streams.

Effect of Oxygen on $NO_x$ Removal

Figure 6:
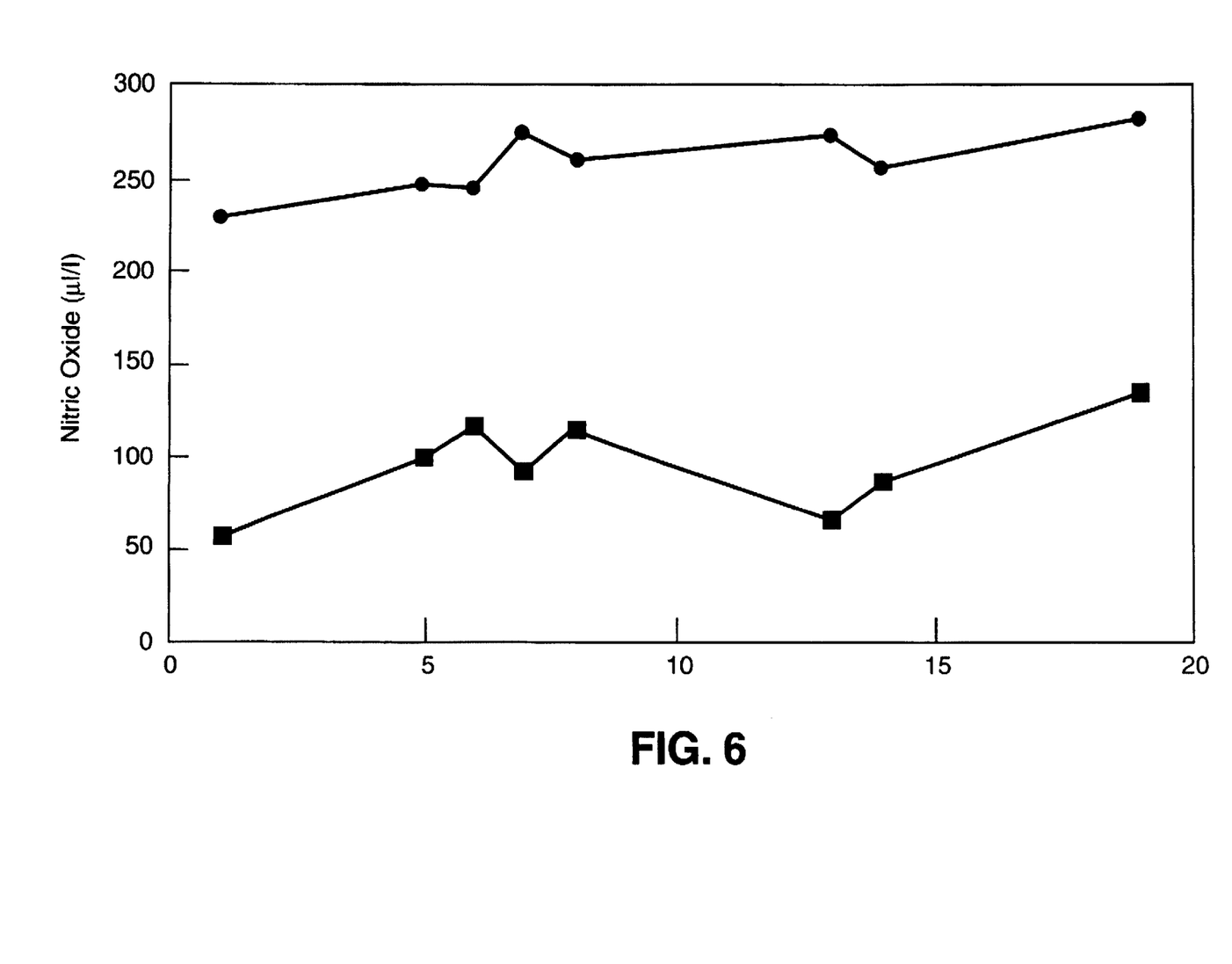
FIG. 6 is an illustrative example of NO, removal from an oxygen-containing polluted gas according to the present invention, wherein ●=inlet NO concentration; ■=outlet NO concentration.

Biofilter 9.0 was constructed with bed medium comprising fresh wood compost and treated with phosphate buffer plus lactate (8 mM $CH_2O$/day) and maintained at 37° C. The influent NO level was maintained at approximately 250 µl/l NO. Initially, the biofilter was operated under anaerobic conditions until a level of NO removal of 87% was achieved. At that time, 0.3% (3000 µl/l) oxygen was added to the $N_2$/NO influent gas stream. Over a 5 day test period, NO removal in the presence of 0.3% oxygen ranged from 71 to 85%. The influent oxygen level was then increased to 1.5% (15,000 µl/l). Within 72 hours, 75% NO removal was measured (FIG. 6). This was surprising since according to the literature, microbial denitrification can take place only under strictly anaerobic conditions. Over a 7 day period, the pH of the biofilter increased from 7.0 to 9.5 while microbial removal of NO in the biofilter decreased to 60%. During this test period, oxygen levels in the inlet and outlet gas streams were monitored by gas chromatography with a Hewlett-Packard Model 5890A (Hewlett Packard, Kennett Square, Pa.). Differences between the inlet and outlet oxygen levels ranged between 0.1-0.3%, indicating that most of the oxygen entering the biofilter was also exiting the biofilter and not simply being scrubbed by organisms residing near the inlet of the biofilter. Thus, these data show that $NO_x$ removal by the naturally occurring mixed culture of denitrifying bacteria in the biofilter occurs in the presence of oxygen, i.e. in an aerobic environment, as well as under anaerobic conditions. The $NO_x$-containing gas stream preferably contains an oxygen content in the range of about 0-5%, and most preferably in the range of about 2.5-5%. The maximum oxygen content at which the biofilters are functional is not presently known, thus the utility of the biofilter at elevated oxygen contents is limited only by its functionality.

I claim:

1. A method of producing a denitrified gas from a gas stream containing nitrogen oxides and optionally up to about 5% oxygen, comprising the steps of:
    (a) providing a biofilter comprising
        a housing comprising an inlet couplable to gas conducting means for receiving the nitrogen oxide-containing gas stream into the biofilter from said gas conducting means and an outlet for removing the denitrified gas out of the biofilter;
        a porous organic filter bed medium disposed in the housing, the bed medium comprising a naturally occurring mixed culture of denitrifying bacteria capable of converting the nitrogen oxides under aerobic conditions to nitrogen gas, carbon dioxide, and water;
    (b) receiving the nitrogen oxide-containing gas stream into the biofilter through the inlet so that the gas stream passes through the bed medium wherein the denitrifying bacteria convert the nitrogen oxides under aerobic conditions to nitrogen gas, carbon dioxide, and water thereby producing a denitrified gas; and
    (c) removing the denitrified gas out of the biofilter through the outlet.

2. The method of claim 1 wherein the bed medium comprises a compost derived from organic matter selected from the group consisting of wood, leaves, grass clippings, and mixtures thereof.

3. The method of claim 2 wherein the bed medium comprises wood compost.

4. The method of claim 2 wherein the bed medium further comprises a member selected from the group consisting of peat, clay, soil, wood chips, wood bark, and mixtures thereof.

5. The method of claim 2 further comprising periodically replenishing moisture to the compost to replace moisture lost by the flow of the gas stream through the biofilter.

6. The method of claim 2 further comprising regulating the pH of the compost.

7. The method of claim 6 wherein the regulating step comprises maintaining the pH of the compost in the range of pH 6–8.

8. The method of claim 7 wherein the step of maintaining the pH comprises adding a buffer solution to the compost.

9. The method of claim 8 wherein the buffer solution comprises a phosphate buffer.

10. The method of claim 7 wherein the step of maintaining the pH comprises adding a member selected from the group consisting of acids and bases.

11. The method of claim 10 wherein the acids are selected from the group consisting of phosphoric acid and lactic acid.

12. The method of claim 10 wherein the bases are selected from the group consisting of potassium phosphate and calcite.

13. The method of claim 2 further comprising providing a carbon source for utilization by the denitrifying bacteria.

14. The method of claim 13 wherein an amount of the carbon source provided is based on the carbon equivalents required by the bacteria to completely convert the nitrogen oxides present in the gas stream to nitrogen gas, carbon dioxide, and water.

15. The method of claim 13 wherein the carbon source is selected from the group consisting of glucose and molasses.

16. The method of claim 13 wherein the carbon source is non-fermentable.

17. The method of claim 16 wherein the non-fermentable carbon source is lactate.

18. The method of claim 2 further comprising regulating the temperature of the biofilter for optimal activity of the denitrifying bacteria in converting nitrogen oxides to nitrogen gas, carbon dioxide, and water.

19. The method of claim 18 wherein the regulating step comprises maintaining the temperature of the biofilter in the range of 15°–60° C.

20. The method of claim 19 wherein the regulating step comprises maintaining the temperature of the biofilter in the range of 22°–37° C.

21. The method of claim 1 wherein the housing is composed of a substantially gas tight material and is constructed to substantially prevent leakage of gas through the housing.

22. The method of claim 1 wherein the nitrogen oxide-containing gas stream contains in the range of about 0–5% oxygen.

23. The method of claim 22 wherein the nitrogen oxide-containing gas stream contains in the range of about 2.5–5%.

24. A biofilter for producing a denitrified gas from a gas stream containing nitrogen oxides and optionally up to about 5% oxygen, comprising a housing comprising an inlet couplable to gas conducting means for receiving the nitrogen oxide-containing gas stream into the biofilter from said gas conducting means and an outlet for removing the denitrified gas out of the biofilter; and a porous organic filter bed medium disposed in the housing so that the nitrogen oxide-containing gas stream passes through the filter bed medium for denitrification, the filter bed medium comprising a naturally occurring mixed culture of denitrifying bacteria for converting the nitrogen oxides under aerobic conditions to nitrogen gas, carbon dioxide, and water.

25. The biofilter of claim 24 wherein the filter bed medium comprises a compost derived from organic matter selected from the group consisting of wood, leaves, grass clippings, and mixtures thereof.

26. The biofilter of claim 25 wherein the filter bed medium comprises wood compost.

27. The biofilter of claim 25 wherein the filter bed medium further comprises a member selected from the group consisting of peat, clay, soil, wood chips, wood bark, and mixtures thereof.

28. The biofilter of claim 24 further comprising a sealable filling port for adding a liquid to the compost and a sealable drain port for draining excess liquid from the compost.

29. The biofilter of claim 24 wherein the housing is composed of a substantially gas tight material and is constructed to substantially prevent leakage of gas through the housing.

30. The method of claim 1 wherein said nitrogen oxide-containing gas stream comprises about 2.5–5% oxygen.

31. The biofilter of claim 24 wherein said nitrogen oxide-containing gas stream comprises about 2.5–5% oxygen.

* * * * *